United States Patent [19]

Hay

[11] Patent Number: 5,355,895
[45] Date of Patent: Oct. 18, 1994

[54] OCULAR DISEASE DETECTION APPARATUS

[76] Inventor: S. Hutson Hay, 310 Clinton Ave. West, Huntsville, Ala. 35801

[21] Appl. No.: 93,685

[22] Filed: Jul. 20, 1993

[51] Int. Cl.⁵ .............................................. A61B 13/00
[52] U.S. Cl. ..................................... 128/745; 351/211
[58] Field of Search ........................... 128/745; 600/27; 351/200, 211, 221

[56] References Cited

U.S. PATENT DOCUMENTS

| | | | |
|---|---|---|---|
| 4,618,230 | 10/1986 | Ens et al. | 128/745 |
| 5,002,385 | 3/1991 | Kasahara et al. | 351/211 |
| 5,099,858 | 3/1992 | Hofeldt | 128/745 |
| 5,120,123 | 6/1992 | Akiyama | 128/745 |
| 5,139,030 | 8/1992 | Seay | 128/745 |
| 5,280,313 | 1/1994 | Kohayakawa | 351/211 |

OTHER PUBLICATIONS

Richez et al. "Suinusoidal light stimulator. . . flicker perception." Med. & Biol. Eng. & Comput. May 1977.

Primary Examiner—Max Hindenburg
Attorney, Agent, or Firm—C. A. Phillips

[57] ABSTRACT

An ocular disease detection device is constructed having a defocusing mechanism that causes eyes of a subject to be defocused. This is primarily accomplished by providing a beamsplitter at a first focal distance from the eyes and projecting an image at a second focal distance to the beamsplitter and then to the eyes. This presents an image having two focal lengths therein to the subject, which defocuses the eyes. A beam generator and camera are mounted so that their respective axes are closely proximate each other and serve to illuminate and receive images of the defocused eyes via the beamsplitter, respectively.

20 Claims, 5 Drawing Sheets

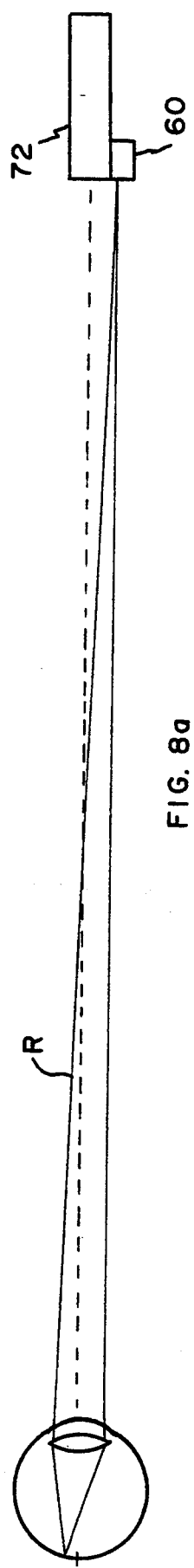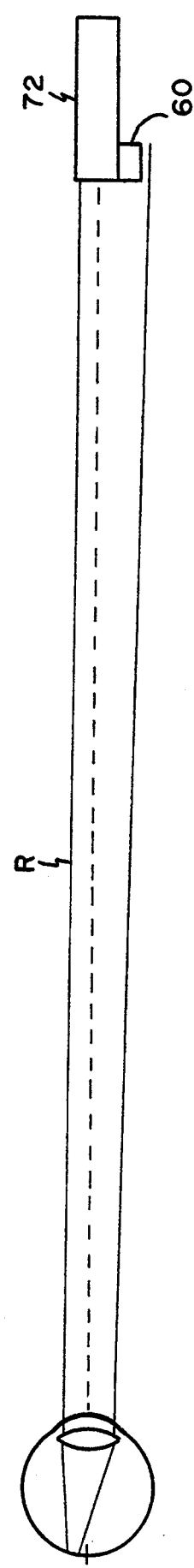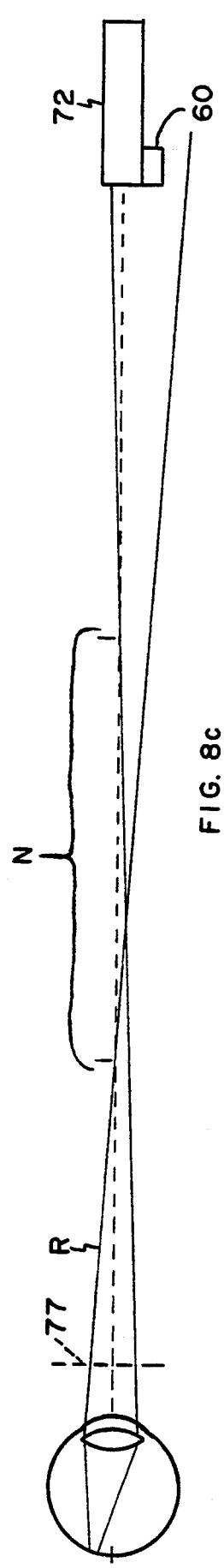

OCULAR DISEASE DETECTION APPARATUS

FIELD OF THE INVENTION

This invention relates generally to devices for detecting optical ocular diseases in the human eye, such as those related to refractive error, opacities of the eyes, and alignment of visual axes of the eyes, and particularly to a compact, portable device of the stated type which defocuses eyes of a subject. This occurs through use of a first visual stimulus at a first focal distance, which also serves as a partially reflective surface, with a second visual stimulus at a second focal distance superimposed on the first visual stimulus. A beam-generating flash unit provides an adjustable beam of light to the eyes, and a CCD camera records an image of the eyes as reflected from the first visual stimulus.

BACKGROUND OF THE INVENTION

In preschool children, detection of maladies of the eyes that cause amblyopia, or strabismus (a deviation of the optical axis of one eye from the optical axis of the other eye), is particularly important. As an untreated child becomes older, neural development in the brain tends to permanently suppress vision in the diseased eye. This prevents proper binocular vision and is irreversible. In order to correct this condition, treatment must begin in the early years of life to be effective. As about five percent of children are either born with or develop strabismus or amblyopia, diagnosis and treatment of this condition at as early an age as possible, preferably prior to about 12 months, is highly desirable. However, considerable difficulty may be encountered in properly administering an ocular screening test to pre-verbal children of such a young age.

Additionally, other conditions of the eyes relating to errors of refraction of the transparent media of the eye, such as nearsightedness (myopia) and farsightedness (hypermetropia), and conditions relating to opacities of the eyes, such as cataracts, scars on the cornea, and tumors, as well as problems such as detachment of the retina, need to be diagnosed and treated so as to provide higher quality vision for the patient.

Screening devices for screening a large number of subjects over a relatively short period of time have been proposed for detecting strabismus and other abnormal conditions of the eyes. These devices function by directing light from a light source to the eyes of a subject, which are fixed and focused at a point defined by a fixation light mounted about one degree off-axis with respect to the light source. Generally, a camera utilizing photographic film is positioned as close as possible to the fixation light. As such, off-axis light from the light source enters the eyes and is refracted by the transparent media, which includes the lens, of each of the eyes.

In an individual with normal eyes, an incoming image of the light source is refracted and perfectly focused as a tiny image upon the retina. As the light is off-axis with respect to an optical axis of the eyes, the tiny image of the light source falls generally on the macula, a pigmented structure of the retina, and the fovea, which is coincident with the optical axis of the eyes. A portion of the light is reflected, generating a retinal reflection, or reflex. This retinal reflection is re-refracted by the lens as it exits the eyes and is collimated, thereby to be directly coincident with respect to light from the light source.

In the individual with normal eyes, the camera records a small, well-defined point of light in the center of the pupil, this point being a reflection from the cornea, or outer transparent covering of the eye. The reflection from the macula is not seen due to the refracted reflection being perfectly focused and directed back toward the light source; however, faint illumination of the macula is observed around the reflection from the cornea due to scattering of light within the eye. This faint illumination of the macula with a small, centered reflection from the cornea is the optical signature of a normal eye.

With the flash positioned above the camera lens and separated from the lens and fixation light by about one degree of angular separation, a nearsighted eye (myopia) refracts the outgoing reflection to be diverging and inverted, as opposed to being collimated. If the angle of divergence of the retinal reflection from the myopic eye is large enough, then a portion of the retinal reflection is intercepted by the camera lens. This results in the camera recording a bright crescent from each eye generally in the lower quadrants of the pupil, the crescents appearing in the lower quadrants due to inversion of the retinal reflection effected by the myopic eye. Of course, the distance between the subject and the flash, fixation light, and camera determines sensitivity of the device, with a longer distance allowing greater divergence of the retinal reflection, meaning that a bright crescent will be recorded at lower errors of refraction of the eyes. Conversely, a shorter distance between the subject and the flash, fixation light, and camera allows less divergence of the retinal reflection, causing the camera to record a bright crescent at higher errors of refraction of the eyes. Generally, and irrespective of the sensitivity of the device, the larger the bright crescent, the greater the severity of nearsightedness.

In the instance where the eyes are farsighted (hypermetropia), the retinal reflections diverge as described and are not inverted as they leave the eyes. As such, the bright crescents appear on the same side of the pupil as the flash with respect to the camera lens. With the flash located above the camera as described, the camera records a bright crescent in the upper quadrants of the pupil. Again, the size of the crescent correlates with severity of the farsighted condition.

In the instance where an individual is afflicted by strabismus, a deviation of the optical axis of one eye with respect to the optical axis of the other eye, the point of light reflected by the cornea in the deviating eye is not equidistant from upper and lower and right and left sides of the eye, as compared with the non-deviating eye. Additionally, the retinal reflection or a portion thereof may appear in the deviating eye as a bright source of light from the pupil.

With respect to astigmatism, which is usually associated with nearsightedness or farsightedness, the crescent will be rotated around edges of the pupil in a positive or negative direction a number of degrees corresponding to the particular combination of the axis and optical power of the astigmatic eyes of that individual.

Opacities of the transparent media of the eyes, such as cataracts or scars on the cornea, produce darkened regions in the reflections wherever they are located.

In some of these devices of the prior art, the fixation light is positioned about 18.9 feet from the subject, a distance such that when the eyes are focused on the fixation light, the optical axes of the eyes are essentially parallel and focused on optical infinity. At this distance, slight divergence of the retinal reflection corresponding to about 0.25 diopters refractive error of the eyes is recorded by the camera. However, size of these devices is a drawback; devices of this length are awkward to handle and move and require a table or support of about 18.9 foot length when in use. Further, since these devices are extremely sensitive to refractive errors, children having only minor refractive error defects of 0.25 or 0.5 diopters and who would derive only dubious benefit from corrective lenses were selected during screening as having defective vision.

Finding the length of these longer screening devices to be cumbersome to move and temporarily install, others have proposed reducing size of these devices by shortening the optical path between the camera, light source, and eyes of the subject. However, when eyes of a subject are focused on a relatively near fixation light, the optical axes of the eyes converge on the fixation light, rotating the retinal reflection about the optical axes of the eyes and causing the appearance of an astigmatic condition. Further, normal convergence of the eyes on a relatively near fixation light prevents differentiation of some ocular misalignment disorders.

One of these proposed screening devices is disclosed in U.S. Pat. No. 4,669,836 to Richardson et. al. and includes a foldable base which, unfolded, measures about 2.4 meters in length. At one end of the base is an upwardly extending head positioning station for positioning the head, and thus eyes, of an individual being screened in relatively precise vertical and horizontal planes. At an opposite end of the device is a camera focused in a plane of the head positioning station. An electronic flash unit is mounted below the camera, and a blinking fixation light to draw the gaze of an individual is mounted just above the camera lens.

Problems with this device are, as stated, its length, which, in spite of the fact that it may be folded for storage or transport, requires that it have in excess of 2.4 meters of unobstructed floor space. When folded, its mass is about 22 pounds. Further, since images of subjects eyes are photographically made on film, there is no immediate feedback as to whether eyes of the subject were correctly positioned, if the test was correctly administered, or if the subject was cooperative in looking at the fixation light, a requisite condition for obtaining a satisfactory screening result. Additionally, since the device is less than half the 18.9-foot length required for a subject to focus his/her eyes on infinity, optical aberrations are introduced in the recorded images due to the eyes converging on the fixation light. This impairs accuracy of the device. Further yet, the bright flash may startle very young children.

A screening device similar to that described in U.S. Pat. No. 4,669,836 is described in a paper entitled "The Remote Sensing of Eye Disorders Utilizing the Retinal Reflex Photometer" by S. Hutson Hay and Rhonda Wharry, which was published in Volume 601, pages 107–111 of the 1985 *Proceedings of The Society of Photo-Optical Instrumentation Engineers* and discloses a device also having a camera and off-axis flash at one end, a fixation light closely proximate the camera, and a head positioning station located 18.9 feet distant at the opposite end of the device. The photographic images may be subjected to limited computer enhancement.

Problems with this device are its length, which requires more than 18.9 feet of unobstructed floor space during use. Additionally, as in the prior device, photographic images are recorded on film which must be developed before the results are obtained. Again, the bright flash may be uncomfortable for small children.

Another paper entitled "Retinal Reflex Photometry as a Screening Device for Amblyopia and Preamblyopic States in Children" by S. Hutson Hay, M.D., Joseph H. Kerr, Robert Rhea Jayrose Jr., Ph.D., James C. White II, and Michael Funke, which was published in the March 1983 edition of the *Southern Medical Journal*, discloses a hand-held camera with a 1,000-mm telescopic lens, with an off-axis flash mounted below the lens. A light-emitting diode (LED) serves as a fixation light and is mounted just above the lens. The subject's head is carefully stabilized 18.9 feet from the lens; and with the subject gazing at the LED, a photograph with simultaneous flash is taken.

Again, this device requires more than 18.9 feet of unobstructed floor space in order to perform the screening, and photographic images are recorded on film which must be processed in order to obtain a result, and the flash may disturb small children.

U.S. Pat. No. 4,989,968 to Howard L. Freedman discloses a camera having an internal light path of about one meter, the light path being folded by mirrors. The camera utilizes a small, slit aperture and a light source positioned 0.5 mm from the slit aperture. Both the slit aperture and the light source are mounted in rotatable relation with the optical axis of the camera so that they may be rotated through at least a 90-degree arc. A series of LED fixation lights, which may be red or any other color, are mounted just below the slit. Provisions are made to place two photographs on a single sheet of self-developing film. Further, a parallax aiming system is provided which projects two light images onto the forehead of the subject and the distance between the subject and camera adjusted until the light images touch, indicating proper alignment and focusing. In use, two photographs are taken of a single subject, the second photograph taken with the slit aperture and light source rotated 90° from a position used to take the first photograph. This allows observation and recording of two discrete meridians of refractive error juxtapositioned 90° with respect to each other.

Problems with this device are that two photographs are required, increasing the probability that the second photograph will be incorrectly taken due to the subject's vision being disrupted by persistence of the image of the first flash. Additionally, the necessity of taking two photographs with accompanying bright flashes in relatively quick succession may cause problems with small children who, after being startled by the flash during the first photograph, may be somewhat less cooperative during the second photograph. Further, it is necessary for an operator of the device to be actively involved with precise focusing and positioning of the camera and rotation of the slit aperture and flash between photographs, this all making for a relatively complicated and trying procedure, especially when groups of very young children, such as in day care centers, are being screened.

Accordingly, objects of this invention are to provide an ocular disease detection device which is relatively compact, occupying in a longest embodiment only about four feet of space in length and about two feet of space in width, and which during use causes the subject's eyes to become defocused as though the subject were looking at a distant object. Additionally, the device of this invention is uncomplicated in its use. Further, the device does not direct a bright flash of light into eyes of those being tested.

SUMMARY OF THE INVENTION

A device for detection of optical ocular diseases is set forth having an eye positioning station which assists in positioning eyes of a subject in a particular focal plane of a camera lens. A relatively broad, featureless first visual field having reflective properties is positioned in front of and at a first discrete distance from said eye positioning station, and superimposed on this visual field is a visual stimulus of varying character at a second discrete distance from the eye positioning station. The visual field and visual stimulus cooperatively serve to defocus eyes of a subject. A light beam generator provides a beam of light for illuminating eyes of a subject, and a camera is positioned to receive a reflected image of the eyes from the visual field.

BRIEF DESCRIPTION OF THE DRAWING

FIG. 8a is a diagrammatic view of the retinal reflection of an eye with no refractive error and relative position of a camera lens and light source of the present invention.

FIG. 8b is a diagrammatic view of the retinal reflection of a farsighted eye and relative position of the camera lens and light source of the present invention.

FIG. 8c is a diagrammatic view of the retinal reflection of a nearsighted eye and relative position of a camera lens and light source and showing a null region.

DESCRIPTION OF THE PREFERRED EMBODIMENT

This device detects and quantifies ocular diseases, particularly cataracts, refractive errors of a selected degree, retinal detachments, alignment disorders, focusing disorders, corneal disease processes, and alterations of media clarity resulting from inflammation or infection. Additionally, macular disease processes that alter the reflective properties of the macula, such as degenerative conditions, infection, inflammation, and tumors of the macular structures are detected. Further, the instant invention may be used to assess adequacy of a prescription of corrective lenses.

As a beam of light is directed into eyes of a subject, an image of the resultant reflection travels along an almost identical path but in a reverse direction as the beam to an image recording and display device. Additionally, by particularly utilizing a beamsplitter and mirrors in conjunction with an image of a dim, indistinct varying light, such as a moving light, an image is presented to a subject that requires the subject to attempt to focus on two discrete visual stimuli at two different focal lengths. Here, a relatively broad, dark, visual field in a first focal plane serves as a first background stimulus, and upon which a second visual stimulus, such as the image of a moving light, is projected from a second, longer focal distance and reflected to the eyes. This causes the subject's eyes to become relaxed and defocused, as though the subject were looking at a distant object, bringing optical axes of the eyes into approximately parallel relation and allowing the lens of each of the eyes to relax to its normal shape. As is well known, the ciliary muscles of the eye serve to thicken the lens in response to focusing at relatively near distances, while allowing the lens to relax to a thinner shape when focused at relatively far distances. This allows the optical and physical length of the invention to be limited to a relatively short length without the results being affected by convergence of the optical axis of the eyes or focusing of the lens therein on a relatively near fixation light. Further, the device of the present invention may be used to compare focusing of the eyes at relatively far and near distances and allows simultaneous evaluation of responses of the eyes at such distances.

Figure 1:
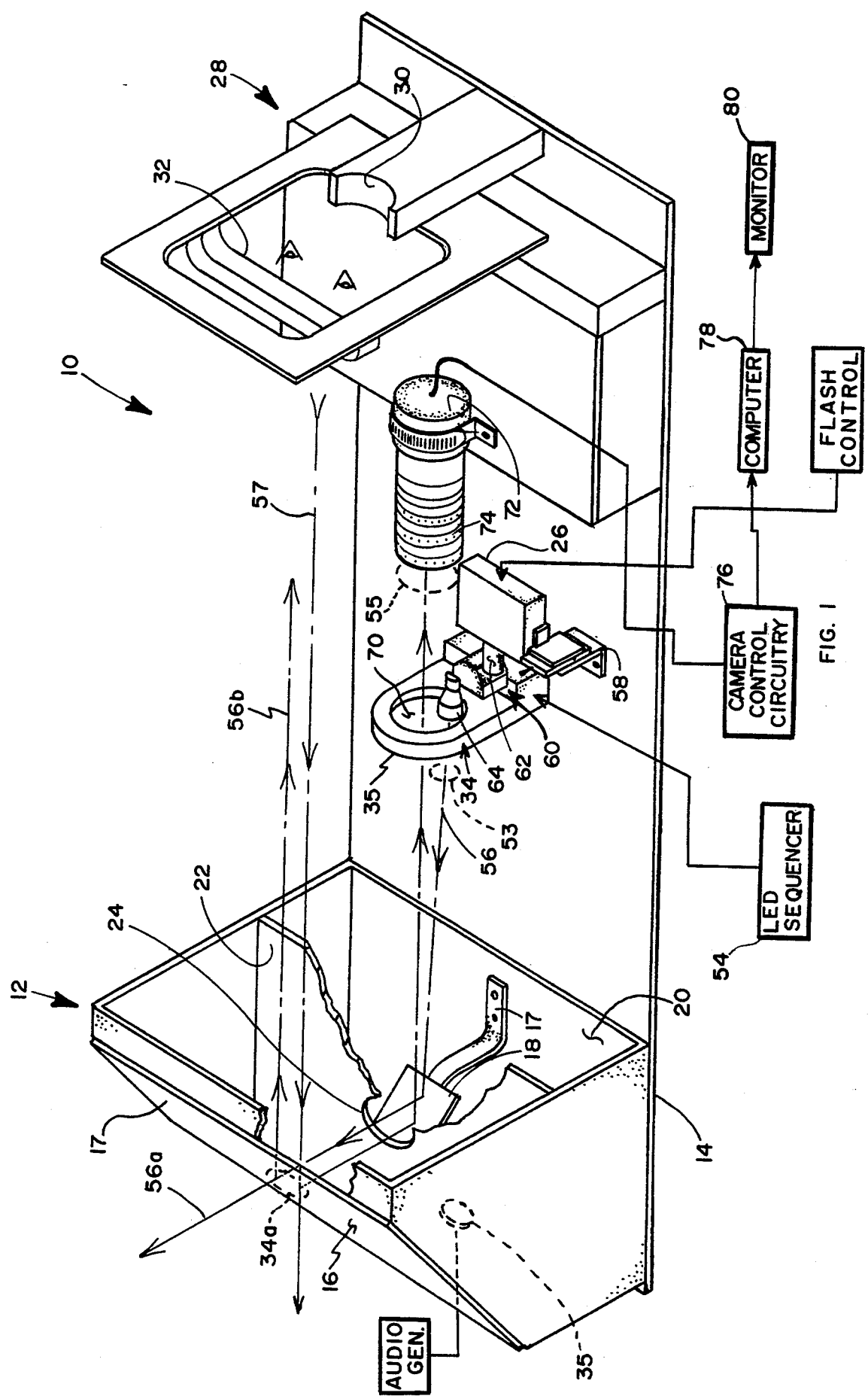
FIG. 1 is a partial pictorial, partial block diagram view of a first embodiment of the present invention.

Referring to FIG. 1, a first embodiment of an ocular diagnostic apparatus 10 of the present invention is shown. Here, an enclosure 12 mounted to a base 14 provides support for a beamsplitter 16, with a bracket 17 supporting a mirror 18 within a lower region of enclosure 12. Beamsplitter 16 is about 15 inches wide and about 12 inches high and may be of a type of plate glass known as MIRROPANE EP TM, manufactured by Libbey, Owen, and Ford, Inc. This type of glass is constructed having a darkly tinted substrate glass having one side coated with a reflective material such that about 60% of light striking the glass is reflected, the combination of the dark tint and reflective coating resulting in transmittance of visible light of about 13%. As such, with the reflective side oriented toward the subject, beamsplitter 16 provides a visual field of a flat, dark, featureless, relatively broad character.

Enclosure 12 is constructed having a generally open front region 20, with beamsplitter 16 mounted over and tilted toward mirror 18. This elevated relation of beamsplitter 16 over mirror 18 allows for construction of a more compact device due to folding of the optical path by mirror 18 and beamsplitter 16. Thus, for an ocular disease detection device having an effective focal length of 2 meters, or 78.75 inches, the device may be constructed of a shorter length of about 1 meter. It is to be noted that this length is the entire focal length of the device and requires only little more than this length when in use. With this length, use of the device may occur in an area no larger than a small storage room or closet, as opposed to a larger area of something in excess of 18.9 feet, as required by at least some of the prior art devices.

A baffle 22 having an opening 24 for passing light and images therethrough is positioned between mirror 18 and beamsplitter 16 and is of a dark, nonreflective color, such as flat black, so as to absorb scattered light and prevent such scattered light from interfering with light reflected to and from beamsplitter 16. Additionally, baffle 22 assists in maintaining the flat, featureless visual character of beamsplitter 16 so that a subject looking at the beamsplitter focuses his/her eyes thereon. Beamsplitter 16 and mirror 18 are positioned as shown about 90° with respect to each other so that a portion of a beam of light or an image entering enclosure 12 and striking beamsplitter 16 is passed to mirror 18 and reflected out of enclosure 12 and a beam of light or an image entering enclosure 12 and striking mirror 18 is reflected to beamsplitter 16 and divided. This is also a feature of the invention, as a beam of light is generated by a flash unit 26, with only a portion of this beam, about 50% to 60%, reflected by beamsplitter 16 to eyes of subjects being screened. As such, beamsplitter 16 reduces intensity of the beam directed into eyes of the subject.

Significantly, beamsplitter 16 is at a first distance, i.e., in a first focal plane, with respect to the subjects eyes and receives an image of a small moving light and reflects this image to the subject's eyes. Thus, the moving light is at a second, greater distance, i.e., a second focal plane, with respect to the subject's eyes. With the subject looking at the flat, featureless expanse of beamsplitter 16 at one focal distance and the projected image of the moving light superimposed on and reflected from beamsplitter 16 at a second focal distance, an optically confusing situation is created that temporarily defocuses the subject's eyes. This defocusing breaks convergence of the eyes and brings them into approximately parallel relation and causes the ciliary muscles to relax, allowing the lens to assume its thinner, relaxed shape, as though the person were looking at something in excess of the focal length of the instant invention.

At the opposite end of base 14 about 38 inches from beamsplitter 16 is a positioning apparatus 28, which serves to position the head and eyes of an individual being screened in a particular focal plane of analysis. Positioning apparatus 28 includes a chin rest 30, which is adjustable by means not shown in order to vertically position the eyes within the area of the beam of light. A stabilizing bar 32 against which the subject places his/her forehead also assists in positioning and stabilizing the head, and thus the eyes, of the individual. Constructed as such, the subject has a relatively wide, unobstructed field of view, with beamsplitter 16 centrally located therein, which is unlike some of the prior art which have small or narrow openings through which the subject is required to peer, causing subtle physiological changes to the eyes that alters accuracy of the device.

For producing an image of the small, moving light which is projected onto beamsplitter 16, and as another feature of the invention, a defocusing light apparatus 34 of annular construction is mounted to base 14 intermediate positioning apparatus 28 and enclosure 12 about 22 inches distant from mirror 18. With mirror 18 mounted about 8 inches below beamsplitter 16, an image of light from light apparatus 34 in a focal plane about 30 inches further than beamsplitter 16 is projected onto beamsplitter 16. As such, from positioning apparatus 28, with the beamsplitter at the first, shorter focal distance, the small, moving image from light apparatus 34 at a second, greater focal distance appears superimposed on beamsplitter 16. This combined image of the beamsplitter at one focal distance and a varying, or moving, light from light apparatus 34 at a second focal distance produces defocusing of the eyes, in contrast to the prior art which uses fixation lights to produce focusing and fixation of eyes of a subject at a particular focal length.

In some applications, as shown in FIG. 1, a second light apparatus 34 or other light emitting device may be mounted to the rearward side 17 of beamsplitter 16 at dashed line position 34a so as to be in the same focal plane therewith. Here, the second light apparatus serves to provide a near fixation point for evaluating refractive error of eyes focused at the near fixation point. In this embodiment, two discrete images of the eyes are taken, one with the eyes defocused by light apparatus 34 and beamsplitter 16 as described, and the other with the eyes focused and fixed on the light apparatus at 34a. The two images of the eyes may then be compared to reveal any difference of refractive error between the eyes in either the defocused and near focused conditions. Tests thus far have revealed at least one young subject whose vision is close to normal in both eyes when focused at the focal plane of beamsplitter 16 (38 inches), but when defocused, as in a far focused condition, one eye is substantially farsighted. While as yet undetermined, it is believed that the inverse condition exists, i.e., a condition wherein both eyes are substantially normal when defocused and one eye having substantially different refractive error than the other eye when focused at a near distance, such as the 38 inches or so to the second light apparatus at 34a. This may occur, for example, if the ciliary muscles of the diseased eye were causing uneven thickening of the lens of that eye or if thickening of the lens of the diseased eye is not commensurate with the shorter focal distance and may cause reading difficulties or disabilities at early ages.

Figure 2A:
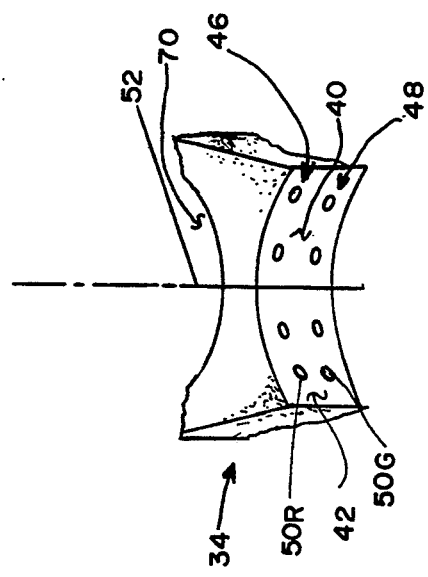
FIG. 2a is a pictorial view of a front and bottom region of the fixation light of the present invention showing relative positioning of LED lights.
Figure 2B:
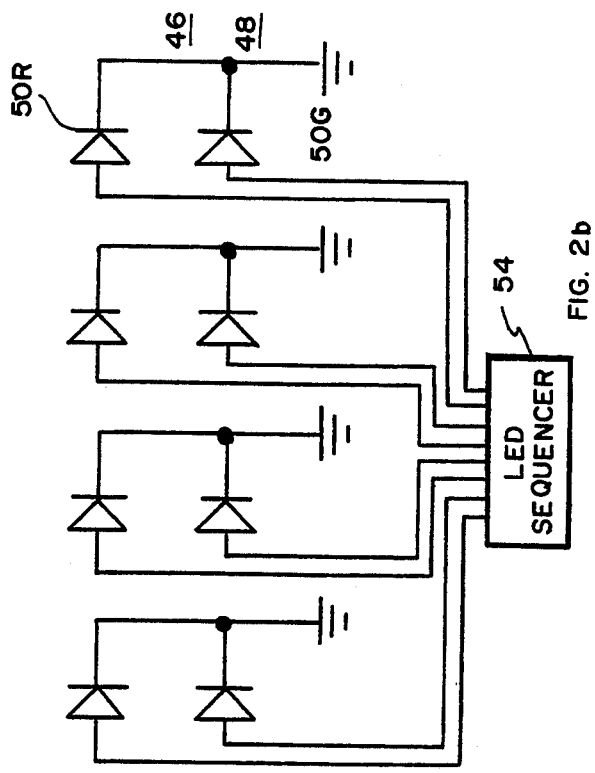
FIG. 2b is a schematic diagram of connections to the LED lights.
Figure 2:
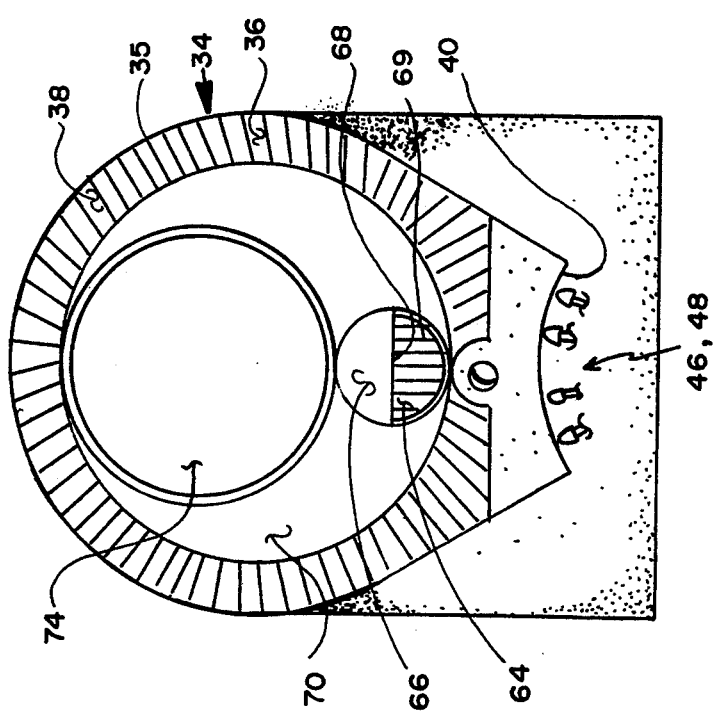
FIG. 2 is a planar view of a front region of a fixation light of the present invention which shows relative positioning of components.

In one embodiment, and as shown in FIG. 2, defocusing light apparatus 34 may be constructed of a conventional ring flash 35, obtainable from most retail photography outlets. Ring flash 35 is provided with an annular light guide 36 about 3.5 inches in diameter and having a circular interior region 70 of about 2.5 inches, with an annular, light emitting front region 38. This region 38 is generally configured to direct light outward from the interior of light guide 36 by a Fresnel TM or other similar type lens configuration. A light-receiving window 40 (FIGS. 2 and 2a) at a bottom of ring flash 35 is provided with a cylindrically concave surface 42 having an axis 52 normal to a plane of the annular portion of ring flash 35, with window 40 adapted to receive light from a flash. Light received by window 40 is channeled to light emitting front region 38, where it is emitted in a forward direction therefrom. It is to be appreciated that a narrow beam of light directed at different positions of inner cylindrical surface 42 of window 40 results in the light emerging from front region 38 at different locations. For example, a small diameter beam of light directed about halfway down a side of window 40 results in a diffuse spot of light emerging about halfway down the same side of front region 38.

Accordingly, for purposes of this invention, and as shown in FIG. 2a, ring flash 35 is modified by locating two rows 46 and 48 of light emitting diodes (LEDs) positioned generally as shown by ovals 50R and 50G such that light from the LEDs is directed into window 40. Particularly, rows 46 and 48 are positioned normal to axis 52 of the cylindrical window 40, with row 46 consisting of LEDs 50R that generate light of red wavelengths and row 48 consisting of LEDs 50G that generate light of green wavelengths. These colors are selected because nearsighted subjects are able to perceive light of the red wavelengths better than other colors, and farsighted subjects are able to distinguish the green wavelengths better than other colors.

The LEDs are illuminated by control circuitry 54 (FIG. 2b) in accordance with a repetitive pattern, such as a pattern wherein the LEDs of one of the rows are sequentially illuminated and then the LEDs of the other row are sequentially illuminated. This may be accomplished, for example, by means of an octal binary sequencer that respectively generates eight sequential binary codes, with eight discrete decoders that in turn each decode a one of the codes and provide power as an output to a respective one of diodes 50R and 50G. This results in diffuse spots of either red or green light which appear to travel around the front portion of ring flash 35, with spots of one color traveling around the ring, and then spots of the other color traveling around the ring. This type of moving light is believed to be particularly attractive and more intriguing to pre-verbal children, who otherwise may be uncooperative in looking at a single steady, or blinking, light. Additionally, it is believed that the apparent movement of the light serves to assist in defocusing the eyes by causing them to attempt fixation, which does not occur due to the optically confusing image of the beamsplitter at one focal distance and the moving light superimposed thereon at a second focal distance. Further, since intensity of light from each LED is relatively low and is further diffused into a larger spot by the optical properties of ring flash 35, the spots of light that travel around ring flash 35 are quite dim, which also assists in defocusing the eyes by presenting relatively diffuse images having indistinct features. As such, the optical axes of the eyes are caused to be parallel, or nearly so, allowing differentiation of disorders related to ocular alignment from normal near convergence of the eyes.

Referring now to FIG. 1, and in addition to light apparatus 34, a source 35 (dashed lines) of audio stimulation, such as a piezoelectric buzzer or speaker coupled to an audio frequency generator, provides an audio stimulation that draws attention of the pre-verbal child, assisting the child in looking at the moving lights. Buzzer or speaker 35 is positioned behind beamsplitter 16 roughly in line with a center region of beamsplitter 16 and positioning apparatus 28 so that sound from buzzer or speaker 35 appears to be proximate the moving lights projected onto beamsplitter 16.

For illuminating the maculas of eyes of a subject being screened and providing a reflection therefrom, a slightly divergent beam of light 56 is directed onto mirror 18, which reflects the beam through opening 24 to beamsplitter 16. Beamsplitter 16 in turn reflects a relatively low intensity beam of light 56b to the subject being screened and passes a portion 56a of beam 56 out of enclosure 12. This assists in preventing an uncomfortable intense beam of light from impinging eyes of the subject, who may be a preschool child easily startled by an intense flash of light from a photographic flash.

Beam 56 is generated by an electronic flash unit 26 mounted to base 14 by means of an adjustable mount 58 positioned behind annular fixation light 34. Flash 26 provides a flash of light similar to a conventional photographic flash, the flash being of a duration of from 0.01 to 0.001 second. For forming and collimating the light into beam 56, a telescopic lens system 60, such as part number 516, available from TASCO, Inc., is fixedly mounted to flash 26 so that an eyepiece 62 of the telescopic lens system receives light from flash 26, with the beam emerging from objective lens 64. This further reduces intensity of the flash, as a relatively small portion of light from the flash actually enters the smaller eyepiece lens and is diffused further as it exits the larger objective lens. Further, lens system 60 is adjustable so as to vary its focal length, which produces a beam which is converging, diverging, or collimated, allowing reconfiguration of the instrument. Normally, for screening purposes, lens system 60 is adjusted to produce a diverging beam, which diverges to about ten inches or so in diameter over the two-meter focal length of the device and which further diffuses light from flash 26. Alternately, the objective lens may be positioned to receive light from flash 26, with the beam emerging from the eyepiece. Here with this reversed configuration, lens system 60 produces a more divergent or convergent beam, allowing the flash and lens system to be located closer to eyes of a subject. This may occur, for instance, where the flash is mounted to direct a beam directly to beamsplitter 16. In this instance, the intensity of light of the beam would be marginally greater than an intensity of light of a beam of the prior described orientation. However, this may be advantageous inasmuch as two discrete illumination levels of the eyes is available with this device. Further, wavelengths of the beam may be altered by positioning color filters, as shown by a dashed line position 53 of a filter placed in front of objective 64, to filter various wavelengths from the beam. This may be done, for example, to accurately define cataracts by using a beam of blue wavelength light, the cataracts preferentially absorbing light of such wavelengths. Further yet, polarizing filters may be used, such as a pair of circularly polarizing filters, one filter at position 53 in front of objective 64 and a second polarizing filter at dashed line position 55 in front of a camera lens 74. Here, polarized light may be filtered by appropriately orienting the polarizing filters.

The beam of light formed and focused by telescopic lens system 60 is directed through a lower portion 70 of annular fixation light 34, as shown in FIG. 2. Thus, when an individual places his/her head in positioning apparatus 28 (FIG. 1) and looks at the reflected image of the moving light from light apparatus 34 from beamsplitter 16, beam 56, when flash 26 is activated, covers about a ten-inch diameter area of analysis which includes the persons eyes and face.

Mount 58 supporting flash 26 is adjustable in fine increments in both horizontal and vertical directions so as to precisely position flash 26 within a range of angular separation of about 0° to 5° with respect to a lower edge 74a of camera lens 74. This allows adjustment of the angular separation between flash 26 and lens 74, which adjusts sensitivity of the device by reducing or increasing angular separation between the flash and the camera lens so that the lens receives a retinal reflection of lesser or greater divergence, respectively. Also, mount 58 may be adjusted so as to tilt flash 26, which in this case may direct a small-diameter beam of light which converges with the axis of lens 74 of camera 72 on eyes of the subject. This feature is used where it is desired to direct the beam directly into eyes of the subject with no angular separation between the light source and the flash, which is useful in diagnosing cataracts or other opacities of the transparent media of the eyes. Further, tilting flash 26 allows adjustment of dynamic range of detection of refractive errors.

While flash 26 and lens system 60 is shown in this embodiment to be mounted intermediate positioning apparatus 28 and camera lens 74, it is to be appreciated that the flash and lens system may be mounted at any point in the optical path between the positioning apparatus and lens 74 and may be mounted behind lens 74 as long as beam 56 is almost coaxial with a reflected image ray 57 of eyes of a subject.

For providing a reference for detecting astigmatism and further blocking a portion of the light of beam 56

(FIG. 2), an upper portion of objective 64 is blocked by an opaque material 66. In a preferred embodiment, about half of the objective is blocked, as by a razor blade, with a straight edge 68 of the blade extending horizontally across the central region of objective 64. While a horizontal edge is shown, edge 68 may extend vertically or diagonally in any reference plane, or edge 68 may be configured in a shape other than a straight edge. Additionally, horizontal edge 68 may be used in conjunction with vertical edges or lines 69, such as those found in a Ronchi rule, which may be obtained from Edmund Scientific Company of New Jersey. This Ronchi rule is similar to an optical grating and has about 50 to 100 vertical lines per inch. In this use, analysis of the retinal reflex using vertical and horizontal lines or edges is provided. Significantly, as shown, edge 68 provides a horizontal reference which may be detected in the retinal reflection, allowing a diagnosis of astigmatism and relative degree thereof to be made. Further, the opaque portion of material 66 blocks about half the light passed through telescopic lens system 60. This further reduces intensity of the light directed into eyes of the subject being screened. Further yet, while sensitivity of the device is described above to be adjustable by angularly varying the beam 56 with respect to image ray 57, sensitivity of the device may also be adjusted by raising or lowering edge 68, which in turn varies angular separation of the beam from edge 68 with respect to image ray 57.

A charge coupled device (CCD) camera 72 (FIG. 1), such as a Model ST-4 Star Tracker imaging camera, available from Santa Barbara Instrument Group, 1482 East Valley Road, Suite 601, Santa Barbara, Calif., and provided with a 55-mm, F1.28 telephoto lens 74, is also mounted to base 14. As stated, a lower edge of lens 74 is generally positioned slightly off axis from about 0° to 5° above telescopic lens system 60 and receives an image through an upper region of annulus 70. By recording an image of the eyes through the annulus of the light apparatus, it is assured that the eyes are fixed directly on the camera lens without the necessity of placing a light directly on the optical axis of the camera lens, which would obscure a portion of the 15 reflection from the eyes.

The CCD camera is particularly sensitive to light and has an ASA rating of about 20,000, which is far more sensitive than any of the photographic film of the prior art. As such, the faint reflection from the retina and reflection of the cornea is easily observable and may be obtained from the relatively dim beam 56 which does not evoke a startle reaction from the subject. While lens 74 and camera 72 are shown mounted above telescopic lens system 60, the camera and lens thereof may be positioned on any side of telescopic lens system 60 as long as the camera receives an image of the eyes through the annulus of the ring flash.

Control circuitry 76 is coupled to camera 72 and is provided with software adapted to control outputs from the picture elements (pixels) of the CCD sensing element of the camera. Control circuitry 76 utilizes a frame grabber to store a video frame of an image, digitizes the image, and provides it as a digital signal to computer 78. Computer 78 in turn is provided with software to enhance the image provided by camera 72 and provides the enhanced image to monitor 80. This image enhancement may be the addition of artificial color wherein brighter portions of the reflection are depicted as white areas, with less intense graduations appearing as red, yellow, and green areas, respectively. Further, artificial topography may be applied to the images from the eyes to vertically plot the relative intensities of light issuing therefrom. In this instance, and in combination with the artificial color scheme, the brightest white areas would extend to a highest level, with the white areas surrounded by lower red areas, in turn surrounded by lower yellow and green areas, respectively. Additionally, pattern recognition software may be employed to recognize signatures of normal eyes and the signatures of a number of commonly encountered problems of the eyes, such as nearsightedness, farsightedness, cataracts, etc.

In preparation for use, computer 78 is activated, and the operating system and software for camera 72, and any other software, are loaded into its internal memory. Annular light apparatus 34 is activated, which projects an image of the circularly travelling spot of light to mirror 18, which in turn reflects this image through opening 24 of baffle 22 to beamsplitter 16. Beamsplitter 16 reflects a portion of the image to head positioning station 28, dimming the lights from the light apparatus by about 40 percent. Flash 26 is activated and readied for the first flash. At this point, illumination of the room wherein the detection device is located is dimmed so as to promote dilation of the subject's pupils and to make the fixation light more visible. The first subject places his/her chin in the chin rest, and the chin rest is adjusted as necessary to place eyes thereof in a plane of analysis.

Typically, the chin rest need only be adjusted once for a particular age group of children or adults. The subject is instructed to look at the moving lights, which as seen projected on beamsplitter 16, are at a different focal distance and are relatively dim and indistinct. Movement of the lights causes eyes of the subject to attempt fixation thereon, but defocusing of the eyes is instead effected by the difference between the focal distances of the beamsplitter and the dim, moving light from light apparatus 34. Flash 26 is then energized to produce a flash, which produces beam 56 from telescopic lens system 60 and which is directed through annulus 70 of ring flash 35. Beam 56 impinges on mirror 18, which reflects the beam through opening 24 of baffle 22 to beamsplitter 16. Beamsplitter 16 reflects a portion 56b of the beam as described to eyes of the subject, generating the reflection from the retina and reflection from the cornea. The reflection from the retina and reflection from the cornea is reflected by beamsplitter 16 through opening 24 to mirror 18, which in turn reflects these eye reflections back toward telescopic lens system 60 and camera lens 74. With the angular separation between the light source and edge of the camera lens adjusted as described to about one degree, and with about two meters between the camera lens and eyes of a subject, the portion of the retinal reflection diverging greater than about $-1.75$ diopters is, in addition to the reflection from the cornea, recorded by camera 72 and digitized by control circuitry 76, with the digitized image provided to computer 78 and displayed on monitor 80. The region between about 0 diopters and $-1.75$ diopters is a "null" region produced by divergence of the retinal reflection being insufficient to be received by the camera lens.

This is shown in FIGS. 8a, 8b, and 8c wherein an eye with no refractive error (FIG. 8a) focuses the retinal reflection R directly back to lens system 60 from where the beam of light emerges. Thus, only scattered light from the retina is received by lens 74 with no direct retinal reflection being captured by lens 74. A farsighted eye (FIG. 8b) produces divergence of retinal reflection R so that as the retinal reflection diverges, that portion of the reflection greater than about 1.75 diopters (dashed lines) is received by camera lens 74 and appears at the lower quadrants of the pupillary opening of the eye. Conversely, the nearsighted eye (FIG. 8c) causes inversion of the retinal reflection R such that the reflection appears at the upper quadrants of the pupillary opening of the eye, after which that portion of the diverging retinal reflection greater than about −1.75 diopters is received by lens 74. Here, a null region N exists between about 0 and about −1.75 diopters wherein divergence of the retinal reflection is insufficient to be received by lens 74.

In the instance where it is desired to detect lesser or greater errors of refractive index of the eyes, the angular separation between beam 56 and the axis of camera lens 74 is decreased or increased, respectively, by vertically adjusting mount 58 or edge 68 as described. Additionally, null region N (FIG. 8c) may be altered by positioning a positive or negative lens 77 (dashed lines in FIGS. 7 and 8c) so that a subject looks through lens 77 at beamsplitter 16. Additionally, the axis of the illuminating beam may be altered by tilting flash 26. This allows for varying sensitivity in detecting nearsightedness than otherwise would be possible.

Figure 3:
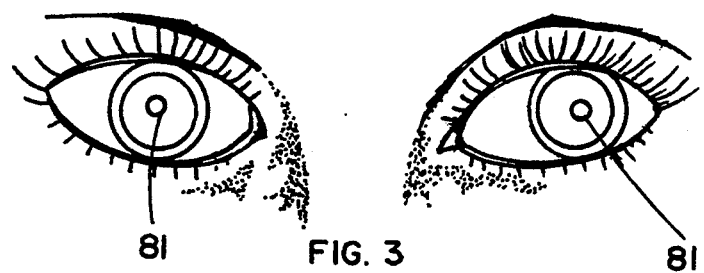
FIGS. 3-6 are illustrations of eyes of subjects recorded by the present invention and having certain disorders.

In this device, a variety of abnormal conditions may be quickly detected and displayed on monitor 80 in real time or stored for later analysis. For instance, diagnosis of strabismus (FIG. 3) is made when the points of light 81 reflected by the cornea are not identically positioned in each eye. Here, the cornea of the deviating eye will reflect a point of light that is not centrally located in the pupillary opening or equidistant from sides of the eye. Refractive error defects of either myopia (nearsightedness) or hypermetropia (farsightedness) produces a reflection on one side of the cornea depending on the focal length of the eye and the position of the light source. In the instant invention, with the light source positioned below the camera lens, nearsightedness (FIG. 4) is indicated when bright portions of the retinal reflection are observed along upper sides of the opening of the pupil. The degree of severity of myopia is indicated by the extent of the illuminated area of the pupil which is visible from the camera, with a larger area indicating a worse condition than a smaller, narrower area. Farsightedness (FIG. 5) is similarly indicated, except the illuminated area occurs along lower sides of the pupil, with degree of severity also indicated by extent of the illuminated area.

Figure 4:
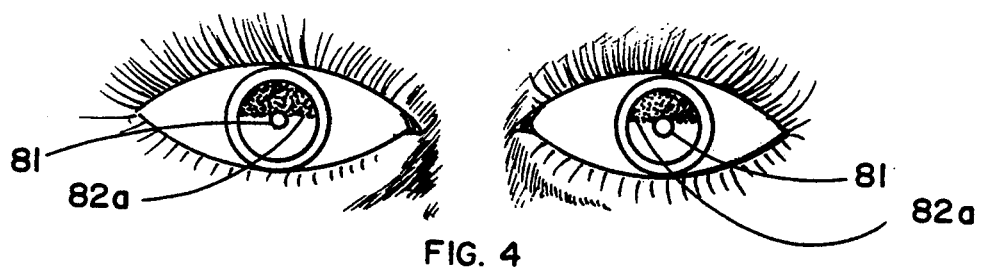
Figure 5:
Figure 6:
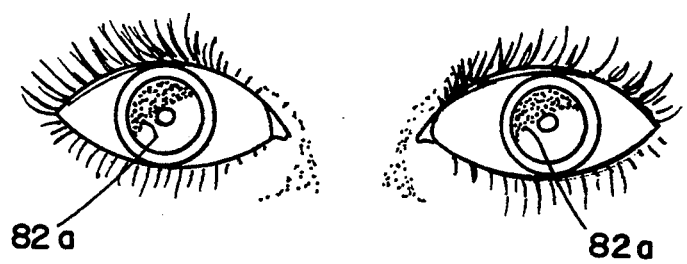

Significantly, the straight edge 68 (FIG. 2) of opaque material 66 across objective 62 is visible in the reflection from the eyes as a horizontal line 82a, as shown in FIGS. 4 and 5. As such, astigmatism, as seen in FIG. 6, which is associated with myopia and hypermetropia, is diagnosed by rotation of the illuminated areas and lines 82a. The direction of rotation correlates with the axis of the astigmatic eye in either a positive or negative direction, with the extent of rotation being a combination of the axis and optical power of the astigmatic eye. Opacities of the eyes, such as cataracts and scars of the cornea (not shown) are evident as dark nebulae and correlate with the position of the cataract. Other types of maladies, such as a detached retina, are generally evident as aberrations in the retinal reflection.

In the instance where adequacy of reflective lenses is to be determined, a subject is entrained to look at the moving light and is photographed as described having the corrective lenses in place. Here, the flash is adjusted so that angular separation between beam 56 and camera lens 74 is slightly less than one degree, wherein the instrument is most sensitive to refractive errors. In the instance where the corrective lenses are adequate, the eyes as seen through the corrective lenses will have the optical signature of normal eyes. Where the corrective lenses are inadequate or too strong, the eyes will have the characteristic pattern of the prevailing refractive error as described.

Figure 7:
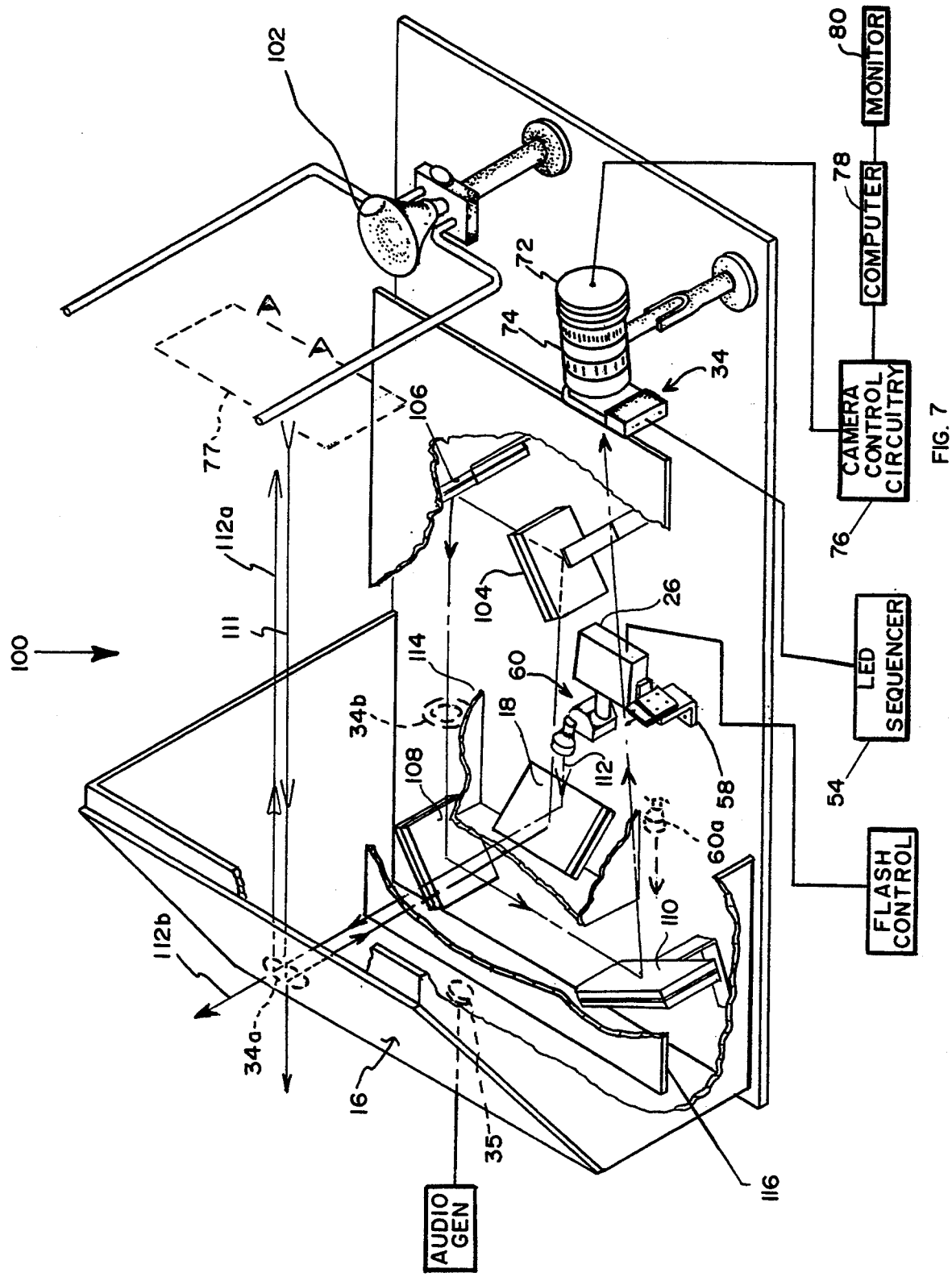
FIG. 7 is a partial pictorial, partial block diagram view partially broken away of a second embodiment of the present invention.

In another embodiment of the invention, as shown in FIG. 7, length of a device 100 constructed in accordance with the principles described above is further shortened to about 24 inches while maintaining a 2-meter focal length of the camera lens. This is accomplished by using a plurality of mirrors to further fold the optical path between the camera and the subject.

In this embodiment, flash 26 is constructed as described in the foregoing having a telescopic lens system 60, a focal length thereof being adjustable to produce a beam that is converging, diverging, or collimated. However, to produce greater divergence of the beam of light over the shorter distance of the device, the eyepiece and objective of telescopic lens system 60 may be reversed as described, with the objective receiving light from flash 26. Alternately, flash 26 may be mounted to direct the beam of light directly onto the beamsplitter (not shown), which reflects the beam to eyes of a subject, or flash 26 may be mounted as shown at dashed line position 60a wherein a lens of lens system 60 passes the beam to mirror 10. Further, as described, the flash and lens system may be mounted at any point between the chin rest and camera.

Light apparatus 34 is constructed as described above from a ring flash, but is conventionally mounted to the lens of camera 72 as shown in FIG. 7. Here, the difference in focal planes between the light apparatus and the beamsplitter from eyes of a subject is about 61.75 inches. With this greater difference of focal lengths between the beamsplitter and light apparatus 34, it is believed that the defocusing effect which breaks convergence of the eyes is increased. Alternately, apparatus 34 may be located at any point between lens 74 and beamsplitter 16, as illustrated at dashed line position 34b, so as to direct an image of a varying light to mirrors 106, 104, and 18 to beamsplitter 16.

A chin rest 102 is positioned as shown at one end of device 100, with beamsplitter 16 located as shown about 17 inches in front of chin rest 102 and tilted as in the prior embodiment to direct an image downward. Mirror 18 is located about 10 inches below beamsplitter 16 and is tilted so as to receive an image from beamsplitter 16 and also receive a reflection from mirror 104, which is located about 9.75 inches toward chin rest 102 from mirror 18. Mirror 104 in turn is angled to direct and receive a reflection to/from mirror 106, which is about 4.5 inches from mirror 104, which reflection takes a path generally normal to the line of sight to beamsplitter 16 from chin rest 102. Mirror 106 in turn directs and receives a reflection to/from mirror 108, which is about 13.5 inches distant from mirror 106. Mirror 108 directs and receives a reflection to/from mirror 110, about 10 inches distant from mirror 108 and in a plane behind beamsplitter 16. Mirror 110 is positioned to direct an image of eyes of the subject to lens 74 of camera 72 and receive an image from fixation apparatus 34. Constructed as such, the focal length from chin rest 102 to lens 74 is about 78.75 inches, or 2 meters, the same focal distance as the prior described embodiment of the invention, which has the advantages as described in the foregoing.

Camera 72 and lens 74 are mounted adjacent to chin rest 102, with the lens angled as shown so that lens 74 is directed at mirror 110. Flash 26 is adjustably mounted as described above to direct the beam to beamsplitter 16 by means of adjustable mount 58, which is adjustable as described so that 0° to 5° of angular separation between an axis of the flash and an axis of the camera lens may be obtained. However, flash 26, if mounted to direct a beam to mirror 110 as described for position 34b, may be tilted to produce divergence of the beam from the retinal reflection to reduce overlap of the beam and retinal reflection on the mirrors, which tends to wash out the image of the retinal reflections. Additionally, when imaging eyes through corrective lenses, the diverging beam from tilted flash 26 impinges the corrective lenses as a slight angle, which otherwise would reflect light back to the camera lens producing a glare from the corrective lenses. Further, filters may be positioned at the camera and flash and lens system for selectively passing selected wavelengths and/or for selectively blocking or passing polarized light. Also, a second light apparatus 34 or the like may be mounted to a rearward side of beamsplitter 16 to provide a near fixation light for reasons described in the foregoing. An audio stimulation device 35 (dashed lines) is positioned behind beamsplitter 16 and operates as described above.

Vertical baffles 114 serve to separate the light path between the mirrors, while a horizontal baffle 116 having an opening as shown by opening 24 (FIG. 1) separates the light path between beamsplitter 16 and the other mirrors. These baffles block scattered and diffracted light which otherwise may interfere and degrade the images passed between the beamsplitter and mirrors.

Function of this embodiment is similar to the above-described embodiment which, after computer 78 and flash 26 are readied as described, the subject places his/her chin in chin rest 102, which is adjusted as described. The subject, if cooperative, is instructed to look at the moving lights; if the subject is a pre-verbal child, he hears the sound from audio stimulator 35, causing the child to look at the moving lights. The effect of looking at objects in two focal planes causes the eyes to be defocused, bringing the optical axes of the eyes into approximate parallel relation and relaxing the lens structure of the eyes, at which point the flash is activated to produce beam 112 from the telescopic lens system 60 of flash 26. Beam 112 impinges upon beamsplitter 16, which passes a portion of the beam 112a to eyes of the subject, with the other, unused portion of the beam 112b passed to infinity. The reflection ray 111 from the eyes, which includes the retinal reflection and any divergence thereof caused by refractive error defects of the lens structure of the eyes, is passed to beamsplitter 16, which passes the retinal reflection back toward the flash. Camera 72 records the image of the eyes, and computer 78 processes images thereof as described above in accordance with its software and provides an enhanced image that may be examined in real time or stored for later analysis. Thus, the enhanced image of eyes of the subject is immediately available so a determination may be made as to whether the subject needs corrective measures to improve his/her vision.

Having thus described my invention and the manner of its use, it is apparent that incidental changes and modifications may be made thereto that fairly fall within the scope of the following appended claims, wherein I claim:

1. An ocular disease detection device comprising:
   eye positioning apparatus for positioning eyes of a subject in a selected focal plane;
   a first, relatively broad, visual stimulus having at least a partially reflective character and generally positioned in front of said eye positioning apparatus at a first focal distance therefrom;
   a smaller, second, visual stimulus of varying character superimposed on said first visual stimulus and appearing at a second focal distance from said eye positioning apparatus, said first and second visual stimulus cooperating to defocus eyes of a subject;
   light beam generation means for generating a beam of light and directing said beam of light to said selected focal plane, illuminating eyes of a subject and producing eye reflections therefrom; and
   visual recording and display means having a lens positioned to receive said eye reflections, for recording and displaying an image of said eye reflections.

2. A detection device as set forth in claim 1 further comprising a third visual stimulus in a focal plane of said first visual stimulus, for providing a near fixation point for eyes of a subject.

3. A detection device as set forth in claim 1 wherein said first visual stimulus comprises a beamsplitter.

4. A detection device as set forth in claim 1 wherein angular separation between said beam of light and said lens is from about 0° to 5°.

5. A detection device as set forth in claim 1 wherein said beam of light is reflected from said first visual stimulus to eyes of a subject.

6. A detection device as set forth in claim 5 comprising at least one mirror positioned to reflect said beam of light to said first visual stimulus.

7. A detection device as set forth in claim 1 wherein said second visual stimulus comprises a light emitting apparatus having an annular light emitting region, and said varying character is movement of a light about said annular region, providing an image of a circularly moving light.

8. A detection device as set forth in claim 7 wherein said lens receives said eye reflections through an interior region of said light-emitting region.

9. A detection device as set forth in claim 1 wherein said light beam generation means comprises:
   flash means for generating a momentary flash of light;
   focusing means for receiving a portion of said light and focusing said portion of said light into a beam of light;
   light intensity reduction means for reducing intensity of said beam of light; and
   reference means for providing a reference indicator in said beam of light, whereby said reference indicator is detectable in said eye reflections.

10. A detection device as set forth in claim 9 wherein said reference means further comprises horizontal and vertical references.

11. An ocular disease detection device comprising:
    eye positioning apparatus for positioning eyes of a subject in a selected focal plane;

moving light generation means having an annular light emitting region, for providing an image of a circularly moving light;

light beam generation means for providing a momentary beam of light;

a beamsplitter in front of said eye positioning apparatus at a first focal distance therefrom and positioned to receive said beam of light and reflect a portion of said beam of light to said eye positioning apparatus and to receive said image of a circularly moving light and reflect said image to said eye positioning apparatus so that said image appears at a second focal distance from said eye positioning apparatus; and a CCD camera positioned off-axis with respect to said beam of light and focused to receive a reflected image of eyes of a subject from said beamsplitter through an interior region of said annular light emitting region;

whereby said beamsplitter at said first focal distance and said moving light generation means at said second focal distance effect defocusing of eyes of a subject.

12. A detection device as set forth in claim 11 wherein said image of a moving light alternates between red and green wavelengths.

13. A detection device as set forth in claim 11 wherein said light beam generation means is adjustable to provide a diverging, collimated, or converging beam.

14. A detection device as set forth in claim 13 wherein said light beam generation means is adjustable to provide variable angular separation between said beam of light and said reflected image.

15. A detection device as set forth in claim 11 wherein said light beam generation means further comprises filter means for filtering said light of said beam.

16. A detection device as set forth in claim 11 wherein said light attenuation means comprises a beamsplitter.

17. A detection device as set forth in claim 16 wherein said beamsplitter reflects about 60% of incident light, reducing intensity of said beam of light.

18. A method for detecting ocular diseases of the eyes comprising the steps of:

(1) positioning eyes of a subject in a focal plane of a camera lens;

(2) providing a flat, generally reflective surface intermediate said camera lens and eyes of a subject so that a light path therebetween is folded, said reflective surface being at a first focal distance from eyes of a subject;

(3) directing a varying image from a second, longer focal distance to said reflective surface and reflecting said varying image to eyes of a subject, causing eyes thereof to become defocused;

(4) directing a beam of light onto said reflective surface and reflecting a portion of said beam to eyes of a subject, generating first eye reflections therefrom;

(5) reflecting said first eye reflections from said reflective surface; and (6) receiving said first eye reflections by said camera lens.

19. A method as set forth in claim 18 further comprising the step of providing a fixation light in a focal plane closely proximate a focal plane of said flat, generally reflective surface, whereby second eye reflections focused on said fixation light are provided.

20. A method as set forth in claim 19 further comprising the step of comparing said first and second eye reflections, for determining if any difference of refractive power exists between the eyes in said first and second eye reflections.

* * * * *